US008697930B2

(12) United States Patent
Bowman et al.

(10) Patent No.: US 8,697,930 B2
(45) Date of Patent: Apr. 15, 2014

(54) CONVERSION OF METHYLAMINE TO OLEFIN OR MIXTURE OF OLEFINS

(75) Inventors: Robert G. Bowman, Woodbury, MN (US); Eric E. Stangland, Midland, MI (US); Rainer Bruening, Leipzig (DE); Angelika Heilmann, Borna (DE); Roland Wagner, Merseburg (DE); Jason Lee Bronkema, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 13 days.

(21) Appl. No.: 13/639,940

(22) PCT Filed: May 31, 2011

(86) PCT No.: PCT/US2011/038489
§ 371 (c)(1), (2), (4) Date: Oct. 8, 2012

(87) PCT Pub. No.: WO2011/159459
PCT Pub. Date: Dec. 22, 2011

(65) Prior Publication Data
US 2013/0079576 A1    Mar. 28, 2013

Related U.S. Application Data

(60) Provisional application No. 61/354,293, filed on Jun. 14, 2010.

(51) Int. Cl.
*C07C 211/03* (2006.01)
(52) U.S. Cl.
USPC ............................ 585/638; 564/478; 564/479
(58) Field of Classification Search
USPC .......... 585/638, 639, 640, 641, 642; 564/478, 564/479, 480; 568/638
See application file for complete search history.

(56) References Cited

U.S. PATENT DOCUMENTS

| 3,636,153 A | 1/1972 | Enders et al. |
| 4,440,871 A | 4/1984 | Lok et al. |
| 4,524,234 A | 6/1985 | Kaiser |
| 4,831,086 A | 5/1989 | Das et al. |
| 4,873,390 A | 10/1989 | Lewis et al. |
| 6,187,983 B1 * | 2/2001 | Sun ................................ 585/638 |
| 7,435,855 B2 | 10/2008 | Bosch et al. |
| 2003/0032848 A1 | 2/2003 | Martens et al. |
| 2007/0287867 A1 | 12/2007 | Zones et al. |
| 2011/0178341 A1 * | 7/2011 | Stauffer ........................ 585/638 |

FOREIGN PATENT DOCUMENTS

| EP | 0893159 A1 | 1/1999 |
| EP | 0993867 A1 | 4/2000 |
| EP | 1790627 A1 | 5/2007 |
| WO | 86/04577 A1 | 8/1986 |
| WO | 98/29363 A1 | 7/1998 |
| WO | 99/02483 A1 | 1/1999 |
| WO | 99/55649 A1 | 11/1999 |
| WO | 00/76944 A1 | 12/2000 |
| WO | 2005/123658 A1 | 12/2005 |

OTHER PUBLICATIONS

Ai-Jie, Chinese Journal of Chemistry, 2005, vol. 23, No. 4, p. 413-417.
Auer, Journal of Molecular Catalysis A, 1999, vol. 141, p. 193-203.
Docquir, Langmuir, 2002, vol. 18, p. 5963-5966.
Jeon, Applied Catalysis A: General, 2006, vol. 305, p. 70-78.
Olah, J. Am. Chem. Soc. 1984, vol. 106, p. 2413-2419.
Sierraalta, Journal of Molecular Catalysis A: Chemical, 2007, vol. 271, p. 185-191.
Thursfield, J Chem. Soc., Faraday Trans., 1998, vol. 94, No. 8, p. 1119-1122.
Roose, Kirk-Othmer Encyclopedia of Chemical Technology, Methylamines, p. 1-16, Nov. 2005.
Turcotte, Kirk-Othmer Encyclopedia of Chemical Technology, Methylamines, vol. 16, p. 355-370, Nov. 2005.
PCT/US2011/038489, International Search Report and Written Opinion of the International Searching Authority.
PCT/US2011/038489, International Preliminary Report on Patentability.
PCT/US2011/038489, Response Written Opinion.
PCT/US2011/038489, Written Opinion of the International Preliminary Examining Authority.
PCT/US2011/038489, Response Second Written Opinion.

* cited by examiner

*Primary Examiner* — In Suk Bullock
*Assistant Examiner* — Sharon Pregler

(57) ABSTRACT

Convert a methylamine (e.g. monomethylamine, dimethylamine and trimethylamine) to a mixture of olefins (e.g. ethylene, propylene and butylene) by placing the methylamine, optionally in a mixture with at least one of ammonia and an inert diluent, in contact with a microporous acidic silicoaluminophosphate catalyst or a microporous aluminosilicate catalyst.

11 Claims, No Drawings

CONVERSION OF METHYLAMINE TO OLEFIN OR MIXTURE OF OLEFINS

This application is a non-provisional application claiming priority from the U.S. Provisional Patent Application No. 61/354,293, filed on Jun. 14, 2010, entitled "CONVERSION OF METHYLAMINE TO OLEFIN OR MIXTURE OF OLEFINS" the teachings of which are incorporated by reference herein, as if reproduced in full hereinbelow.

This invention relates generally to a process for preparing an olefin and more particularly to a process that converts a methylamine to an olefin or a mixture of two or more olefins, especially with a microporous solid acid catalyst.

Several references (e.g. United States Patents (US) U.S. Pat. No. 4,524,234, U.S. Pat. No. 4,873,390, U.S. Pat. No. 4,831,060, European Patent Application (EP) 1790627A1, and Patent Cooperation Treaty Application (WO) 1998/029363) teach multi-step processes or portions of a process for synthesizing olefins from methane. The multi-step processes include several intermediate steps which can include a) conversion of methane to syngas (a step which requires the use of air, or oxygen from air separations or other suitable source), b) conversion of syngas to methanol or a mixture of homologous alcohols (e.g. two to twelve carbon atom ($C_2$ to $C_{12}$) alcohols), and c) direct conversion of methanol to olefins or alternatively conversion of methanol to a higher alcohol in a homologous series (e.g. $C_2$ to $C_{12}$ alcohols), followed by d) dehydration of such higher alcohol(s) to corresponding olefins (e.g. ethanol to ethylene or propanol to propylene). These multi-step processes necessarily require elimination of water from an oxygenate (e.g. $C_2$ to $C_{12}$ alcohol) to yield a final hydrocarbon product. This water contains the oxygen added in step a) necessary to activate methane and its removal represents a lost process value as conversion of the water back to a reactive oxygen species for use in step a) is not economically prudent.

In some aspects, this invention is a process for preparing an olefin or mixture of olefins, which process comprises placing at least one methylamine selected from monomethylamine, dimethylamine and trimethylamine, optionally in a mixture with at least one of ammonia and an inert diluent, in contact with at least one microporous acidic silicoaluminophosphate catalyst or microporous aluminosilicate catalyst under conditions of temperature, pressure and weight hourly space velocity sufficient to convert at least a portion of the methylamine to a product stream comprising a mixture of olefins that comprises ethylene, propylene and butene. The mixture of olefins may contain one or more other olefins such as pentene, hexene, heptene or octene. The process is preferably a gas phase process. This process leads to formation of ammonia as a byproduct which, in some aspects can be captively utilized or recycled in the process of this invention.

In some aspects, this invention includes a precursor process for converting methane to a methylamine.

This invention provides an alternate route to olefin synthesis that avoids production of syngas as a costly intermediate step. It allows for use of methane, a widely available resource, as a raw material for such olefin synthesis. The olefins that result from this invention have utility in a variety of applications, one of which is preparation of a polyolefin such as polyethylene where the olefin is ethylene.

The above conditions include a temperature within a range of from 400° C. to 700° C., preferably from 450° C. to 650° C. When using silicoaluminophosphate (SAPO) catalysts such as SAPO-34, the temperature is more preferably from 450° C. to 550° C. When using aluminosilicates catalysts like ZSM-5, the temperature is more preferably from 500° C. to 600° C.

Such conditions also include a pressure, sometimes referred to as "total system pressure" within a range of from greater than or equal to 0.1 bar (10 kilopascals (KPa)) to 60 bar (6 megapascals), preferably from 1 bar (100 KPa) to 5 bar (500 KPa).

The conditions further include a weight hourly space velocity (WHSV), with respect to methylamine, within a range of from 0.1 grams of methylamine per gram of catalyst per hour to 50 grams of methylamine per gram of catalyst per hour, preferably from 0.5 grams of methylamine per gram of catalyst per hour to 5 grams of methylamine per gram of catalyst per hour.

The conditions may also include use of an inert diluent, preferably nitrogen or methane, with the diluent being present in a mole ratio of diluent to methylamine that falls within a range of from greater than or equal to 0:1 to 20:1, preferably 0:1 to 9:1.

The catalyst is suitably a microporous acidic SAPO catalyst, an aluminosilicate catalyst, or a mixture of a SAPO catalyst and an aluminosilicate catalyst. Preferred SAPOs include SAPO-34 and preferred aluminosilicates include ZSM-5, mordenite, beta, Linde-type L, faujasite, offretite, and ferrerite. More preferred aluminosilicates include ZSM-5 and offretite.

During the course of the reaction, certain catalysts can show deactivation, that is the loss of conversion of methylamine to olefins. If desired, this deactivated catalyst may be regenerated to its initial activity via conventional procedures such as oxidation in air or some other suitable oxidant.

The above process optionally includes a co-feed of ammonia. When present, the co-feed of ammonia provides an amount of ammonia sufficient to alter a ratio of ethylene to propylene in the mixture of olefins, preferably to reduce the ratio of ethylene to propylene relative to the ratio of ethylene to propylene in the absence of ammonia. When present, the amount of ammonia relative to total amine feed is preferably within a range of from 0:1 to 9:1, more preferably from 0.1:10 to 0.5:1.

One may also alter the ratio of ethylene to propylene by modifying reaction parameters. For example, a decrease in reaction temperature leads to a decrease in the ethylene to propylene ratio whereas a decrease in WHSV leads to an increase in the ethylene to propylene ratio. The ratio altering techniques described herein may be used singly or in combination.

For the above process, one preferably uses a mixture of two or more methylamines rather than pure monomethylamine. The mixture has a higher ratio of carbon to nitrogen than pure monomethylamine. The higher ratio tends to improve or increase overall selectivity to ethylene and propylene relative to selectivity to ethylene and propylene when using only monomethylamine.

If desired, one can recycle one or more of unreacted a methylamine, a diluent and ammonia and mix it with fresh methylamine before the mixture contacts the catalyst. There is no need to separate components from, or clean, a recycle feed other than an expected inert purge. As a variation, one can also use some or all of the ammonia, the methylamine(s) or both the ammonia and the methylamine(s) to activate methane in production of methylamine or an intermediate that is later converted to methylamine.

A comparison of the multi-step process noted above, where one must eliminate water, with this invention, where no water is produced is represented as follows:

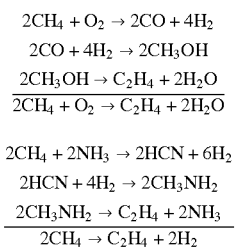

In the process of this invention, one may use a single methylamine, e.g. any of monomethylamine, dimethylamine or trimethylamine, or a mixture of two or more of such methylamines. One may also use any source of methylamine or methylamine mixtures.

U.S. Pat. No. 7,435,855 (Bosch et al.), WO 99/02483 (Corbin et al.), and US 2007/0287867 (Zones et al.) all relate to synthesizing methylamines by reacting methanol, dimethyl ether (DME) or both methanol and DME with ammonia ($NH_3$) in the presence of a catalyst. Bosch et al. uses a heterogeneous catalyst; Corbin et al. uses an acidic zeolite chabazite catalyst; and Zones et al. uses a molecular sieve SSZ-75 catalyst.

European Patent Publication (EP) 0893159 (Hidaka et al.) teaches a silica-modified silicoaluminophosphates catalyst and its use in, for example, producing methylamines through a reaction of methanol with ammonia, dimethylamine through a disproportionation reaction of monomethylamine, and production of lower olefins from methanol. The '159 publication provides extensive listings of molecular sieves especially silicoaluminophosphates (SAPO) in paragraph [0017] (e.g. SAPO-5, 11, 17, 18, 26, 31, 33, 34, 35, 42, 43, 44, 47 and 56) and aluminosilicates such as chabazite, mordenite, erionite, ferrierite, epistilbite, clinoptilolite, paulingite, phillipsite, levynite, zeolite-A, RHO, ZK-5, FU-1, and ZSM-5.

EP 0993867 (Hidaka et al.) provides teachings about preparation of methylamines, particularly dimethylamine, using silica-modified silicoaluminophosphate catalysts such as a SAPO-34 molecular sieve in cubic form, especially H-type SAPO-34. The SAPO-34 catalyst may be modified with any of a number of listed metals or metal compounds such as alkali metals, alkaline earth metals and Group VIII (Periodic Table of the Elements) elements.

J. Chem. Soc, Faraday Trans 94 (1998) pages 1119-1122 (Thursfield et al.) discusses conversion of methanol and $NH_3$ to a methylamine over H-SAPO-34 and zeolite H-RHO microporous catalysts. Thursfield et al. refer to earlier work using various zeolites including ZSM-5. mordenite, erionite, zeolite Y, RHO and ZK-5 as well as SAPO-5 catalysts.

Appl Catal. A 305(2006) pages 70-76 (H. Jeon et al.) evaluate small pore aluminosilicates zeolites (levyne, MCM-35, sigma-1, UZM-5, SSZ-13, SSZ-16, and RHO) together with silicoaluminophosphates analogs (SAPO-35, SAPO-35 and SAPO-56) of some of these zeolites in synthesizing methylamines.

Langmuir 18 (2002), pages 5963-5966 (F. Docquir et al.) presents an infrared study on the adsorption behavior of methylamine in a series of large pore cationic zeolites.

Chinese Journal of Chemistry 23 (2005), pages 413-417 (Han et al.) summarizes an investigation of adsorption of methylamine on highly siliceous MFE, FAU and FER-type zeolites.

Journal of Molecular Catalysis A 271 (2007), pages 185-191 (Sierraalta et al.) discusses gallium-exchanged silicoaluminophosphates catalysts (Ga/SAPO-11) and their interaction with molecules such as ammonia, sulfur dioxide, and methylamine. Ammonia and methylamine adsorption on the Ga/SAPO-11 catalyst are exothermic.

Journal of Molecular Catalysis A 141 (1999), pages 193-203 (Gredig et al.) relates to production of methylamines from carbon dioxide, hydrogen and ammonia on supported copper (Cu) and palladium (Pd) catalysts.

For Examples (Ex) and Comparative Examples (CEx) below, evaluate conversion of methylamine to an olefin mixture using a micro-reactor that has an inner diameter of 10 millimeters (mm) and a length of 300 mm and is connected to a source of gaseous methylamine and a source of gaseous nitrogen. Fill the bottom of the micro-reactor with silicon carbide as an inert material, place a desired amount of catalyst on top of this silicon carbide material, and fill the remaining portion of the micro-reactor above the catalyst with silicon carbide. Use a back pressure valve to regulate internal reactor pressure at 1.5 bar ($1.5 \times 10^5$ pascals (Pa)). Transfer products from the reactor via heated lines to two online gas chromatographs (GCs). One GC analyzes amines with a VARIAN™ CP-Sil 8CB column and a flame ionization detector (FID). The second GC is a micro-GC with two columns (PoraPLOT™-U and alumina/sulfur) and two thermal conductivity detectors (TCDs) to analyze hydrocarbons.

During the reaction of methylamines, the various methylamines can interconvert with one another forming a complex mixture of amines. These amines may become in equilibrium with one another at the temperature of analysis. For example, pure monomethylamine, when fed to the reactor, may be partially converted to olefins, while the remaining unconverted monomethylamine feed is interconverted to a mixture of monomethylamine, dimethylamine, and trimethylamine. For the purpose of the following examples, conversion is calculated on only the fraction of initial feed that is converted to $C_2$ or greater carbon number products (not dimethylamine or trimethylamine), and likewise selectivity is calculated assuming that any interconverted amine does not represent a product of reaction.

Ex 1

Use the above described reactor system, SAPO-34 as catalyst, 491 degrees centigrade (° C.) as a reaction temperature, a weight hourly space velocity (WHSV) of 2 grams of monomethylamine per gram catalyst per hour ($hr^{-1}$), a feed dilution ratio of 9 parts by volume (ppv) of nitrogen per ppv of monomethylamine, and a reactor pressure of 1.5 bar (150 KPa) to effect conversion of the methylamine to olefins. After 40 minutes (min) reaction time, conversion yields a product stream with an ethylene selectivity of 45 percent (%) and a propylene selectivity of 31%.

Prepare the SAPO-34 catalyst used in this Ex 1 following the teachings of U.S. Pat. No. 4,440,871 (Lok et al.). In a typical synthesis of approximately 35 g of SAPO-34, prepare an initial mixture by adding, with stirring, 82 g of aluminum isopropoxide (Aldrich) to 46 g of 85 wt % $H_3PO_4$ (Aldrich) in 104 g of deionized water (DI). To the initial mixture, add, with stirring, 12 g of 30 wt % $SiO_2$ (Aldrich, Ludox AS-30) and 5 g of DI to form a homogeneous mixture. To the homogeneous mixture, add, with stirring, 168 g of 35 wt % tetraethylammonium hydroxide (TEAOH) (Aldrich) to form a reaction mixture. Transfer the reaction mixture to a 600 milliliter (ml) TEFLON™ lined stainless steel autoclave and heat the autoclave and its contents in an oven at 200° C. at autogeneous pressure for 120 hours. Remove the autoclave contents (solid product SAPO-34) by centrifugation, wash the contents with DI, dry the washed contents in air at 100° C., then calcine the dried and washed contents at 585° C. in air for 4 hours (hr) and press the calcined contents to 20 mesh ((941 micrometer (μm) to 50 mesh (290 μm) for use.

Ex 2

Replicate Ex 1, but change the reaction temperature to 550° C. and the catalyst to H-ZSM-S (commercially available from Süd Chemie under the trade designation MFI-H Si/Al2=90) with a $SiO_2/Al_2O_3$ molar ratio of 90. The ethylene and propylene selectivities are, respectively, 10% and 22%.

Ex 3

Replicate Ex 1, but change the reaction temperature to 486° C., the amine to trimethylamine (TMA) and the WHSV to 1.3 $hr^{-1}$ to keep the carbon WHSV constant compared to 2 $hr^{-1}$ monomethylamine feed. After 60 min reaction time, conversion yields a product stream with an ethylene selectivity of 61 percent (%) and a propylene selectivity of 31%.

Ex 4

Replicate Ex 2, but change the amine to dimethylamine and the WHSV to 1.5 $hr^{-1}$ to keep the carbon WHSV constant compared to 2 $hr^{-1}$ methylamine feed. The ethylene and propylene selectivities are, respectively, 10% and 22%.

Ex. 5

Replicate Ex 4, but change the reaction temperature to 547° C., the amine to trimethylamine and the WHSV to 1.3 g of trimethylamine per g of catalyst per hour.

CEx. A

Replicate Ex 2, but change the reaction temperature to 492° C. At this temperature, no conversion of monomethylamine occurs with H-ZSM-5.

Ex 6

Replicate Ex 1, but change the reaction temperature to 469° C.

Ex 7

Replicate Ex 1, but change reaction temperature to 512° C.

Ex. 8

Replicate Ex 1, but change the reaction temperature to 482° C., the amine to dimethylamine and the WHSV to 1.5 g of dimethylamine per g of catalyst per hour ($hr^{-1}$). In contrast to CEx A, use of a SAPO-34 catalyst provides discernible conversion at a temperature as low as 482° C., a temperature lower than 492° C. at which no conversion occurs with H-ZSM-5 catalysts.

Ex. 9

Replicate Ex 2, but change the reaction temperature to 580° C., and the amine to a 1:1:1 molar mixture of monomethylamine, dimethylamine, and trimethylamine

Ex. 10

Replicate Ex 2, but change the catalyst to H-ZSM-5 provided by Zeolist International (CBV 5524G) with $SiO_2/Al_2O_3$ ratio of 25.

Ex. 11

Replicate Ex 2 but change the catalyst to H-ZSM-5 provided by Zeolist international (CBV 28104) with $SiO_2/Al_2O_3$ ratio of 140.

Ex. 12

Replicate Ex 2, but change the catalyst to a LTL catalyst (commercially available from Engelhard under the trade designation EZ 200),

Ex. 13

Replicate Ex 2, but change the catalyst to offretite (commercially available from Toyo Soda Co. Ltd. under the trade designation TSZ-520), and the reaction temperature 541° C.

Ex. 14

Replicate Ex 2, but change the catalyst to a faujasite catalyst (commercially available from Tosoh Co. under the traded designation HSZ-320), and the reaction temperature 544° C.

Ex. 15

Replicate Ex 5, but change the catalyst to a mordenite catalyst (commercially available from Toyo Soda Co. Ltd. under the traded designation TSZ-640), and the reaction temperature 546° C.

Ex. 16

Replicate Ex 5, but change the catalyst to a Linde-type 13X catalyst (formerly commercially available from Union Carbide under the traded designation ZLD-4000), and the reaction temperature 543° C.

TABLE 1

Conversion and Selectivity Data for Reaction of Methylamines over Various Catalysts

| Ex./CEx | Catalyst | Feed Amine Conversion (%) | Time-on-stream* (min) | Carbon Selectivity** to Ethylene (%) | Carbon Selectivity** to Propylene (%) | Carbon Selectivity** to $CH_4$ and $C_4^-$ hydrocarbons*** (%) | Carbon Selectivity** to $C_4^+$ hydrocarbons**** (%) |
|---|---|---|---|---|---|---|---|
| 1 | SAPO-34 | | 40 | 45 | 31 | | |
| 2 | H-ZSM-5 | | | 10 | 22 | | |

TABLE 1-continued

Conversion and Selectivity Data for Reaction of Methylamines over Various Catalysts

| Ex./CEx | Catalyst | Feed Amine Conversion (%) | Time-on-stream* (min) | Carbon Selectivity** to Ethylene (%) | Carbon Selectivity** to Propylene (%) | Carbon Selectivity** to $CH_4$ and $C_4$- hydrocarbons*** (%) | Carbon Selectivity** to $C_4^+$ hydrocarbons**** (%) |
|---|---|---|---|---|---|---|---|
| 3 | SAPO-34 | | 60 | 61 | 31 | | |
| 4 | H-ZSM-5 | | | 10 | 22 | | |
| 5 | H-ZSM-5 | 69 | 150 | 11 | 23 | 16 | 50 |
| A | H-ZSM-5 | 0 | 175 | 0 | 0 | 0 | 0 |
| 6 | SAPO-34 | 37 | 114 | 55 | 39 | 6 | 0 |
| 7 | SAPO-34 | 85 | 18 | 65 | 27 | 8 | 0 |
| 8 | SAPO-34 | 95 | 38 | 61 | 32 | 7 | 0 |
| 9 | H-ZSM-5 | 71 | 150 | 12 | 17 | 10 | 61 |
| 10 | H-ZSM-5 | 95 | 11 | 17 | 17 | 10 | 56 |
| 11 | H-ZSM-5 | 26 | 200 | 8 | 16 | 16 | 60 |
| 12 | LTL | 82 | 6 | 12 | 8 | 17 | 63 |
| 13 | Offretite | 88 | 6 | 29 | 12 | 5 | 54 |
| 14 | Faujasite | 73 | 6 | 4 | 13 | 20 | 63 |
| 15 | Mordenite | 83 | 6 | 20 | 10 | 5 | 65 |
| 16 | 13X | 15 | 6 | 4 | 5 | 14 | 77 |

*Time of maximum selectivity to ethylene;
**selectivity calculated excluding amine-scrambling reactions;
***butylene (all isomers) and butanes;
****these products were not specifically detected in the product analytical method and are assumed based on mass balance.

The data of Table 1 demonstrate several points. Ex 1 through Ex 5 show that one can convert a methylamine (monomethylamine, diemethylamine or trimethylamine) to a product stream containing ethylene and propylene using a SAPO-34 or H-ZSM-5 catalyst. Under the conditions shown in Ex 1 through Ex 5, SAPO-34 leads to higher conversions of methylamines and higher selectivity to the desired olefins than H-ZSM-5. Ex 1 through Ex 5 also show that SAPO-34 yields more ethylene than propylene whereas H-ZSM-5 yields more propylene than ethylene. CEx A demonstrates that at reaction temperature of 492° C. no conversion to the desired olefins occurs with H-ZSM-5 as a catalyst. This contrasts with teachings related to conventional methanol to olefins technology where such a temperature and catalyst combination leads to a discernible product yield.

In Table 1, H-ZSM-5 Ex 2, Ex 10 and Ex 11 show the effect of changing $SiO_2:Al_2O_3$ ratios in the H-ZSM-5 catalyst. The data show that conversion percentage is related to $SiO_2:Al_2O_3$ ratio, with lower ratios resulting in higher methylamine conversion. From Ex 2, Ex 10 and Ex 11, it appears that lower $SiO_2:Al_2O_3$ ratios lead to higher ethylene selectivity as compared to higher $SiO_2:Al_2O_3$ ratios.

In Table 1, time on stream (time of maximum selectivity to ethylene) for SAPO-34 catalysts is a reflection of catalyst life or rate of catalyst deactivation. With monomethyl amine, the SAPO-34 catalyst in Ex 1 at 491° C. has a time on stream of 40 minutes, with the same feed with SAPO-34 at 512° C. (Ex 7) the time on stream is 18 minutes. At a lower temperature, 469° C. in Ex 6, the time on stream is 114 minutes. The lifetime of the catalyst is progressively shorter at increasing temperatures, while the conversion of methylamines is higher at higher temperatures.

SAPO-34 Ex 1, Ex 6, and Ex 7 also show effects of increasing temperature on selectivity, with an increase in temperature over the range of 469° C. to 512 C providing a corresponding increase in selectivity to ethylene, and a corresponding decrease in selectivity to propylene.

Ex. 12 to 16 show that alternative silico-aluminum crystallite structures, specifically LTL, offretite, faujasite, mordenite and 13X as also function as methylamine conversion catalysts. Similar results are expected with ferrerite.

Ex. 17

Replicate Ex 1, but change the reaction temperature to 490° C., vary the methylamine as shown in Table 2 below and, where indicated, add co-feed of ammonia, to effect a series of nine methylamine to olefin conversions. In Table 2, $NH_3$ represents ammonia, MMA represents monomethylamine, DMA represents dimethylamine, TMA represents trimethylamine, hydrocarbon C:N ratio represents a molar ratio of methyl groups to nitrogen (e.g. DMA with two methyl groups and one nitrogen has a hydrocarbon C:N ratio of 2), and feedstream N:C ratio represents a molar ratio of nitrogen atom to carbon atom in the feedstream. As shown in a comparison of Runs 1 and 3, the presence of $NH_3$ increases the whole or feedstream N:C feed ratio. Choose a WHSV for each run so as to keep carbon based WHSV constant compared to a monomethylamine feed of 2 $hr^{-1}$. For an ammonia cofeed, ammonia partially substitutes for the nitrogen diluent so that the carbon WHSV as well as total flow through the reactor are not influenced by the ammonia addition. In Table 2 the $C_2/C_3$ olefin product ratio is taken at time of ethylene selectivity maximum.

TABLE 2

| Run Number | $NH_3$ | MMA | DMA | TMA | Hydrocarbon C:N ratio | Feedstream N:C ratio | $C_2/C_3$ olefin product ratio |
|---|---|---|---|---|---|---|---|
| 1 | 0 | 0 | 0 | 1 | 3:1 | 0.33:1 | 2.94 |
| 2 | 0 | 0 | 1 | 0 | 2:1 | 0.5:1 | 2.83 |
| 3 | 1.6 | 0 | 0 | 1 | 3:1 | 1.87:1 | 2.48 |
| 4 | 0 | 1 | 0 | 0 | 1:1 | 1:1 | 2.92 |
| 5 | 2 | 0 | 0 | 1 | 3:1 | 1:1 | 2.3 |
| 6 | 2 | 1 | 0 | 0 | 1:1 | 3:1 | 1.79 |
| 7 | 12 | 0 | 0 | 1 | 3:1 | 4.33:1 | 1.43 |
| 8 | 27.3 | 0 | 0 | 1 | 3:1 | 9.43:1 | 1.36 |
| 9 | 8.5 | 1 | 0 | 0 | 1:1 | 9.5:1 | 1.57 |

Ex. 18

Replicate Ex 1 at a reaction temperature of 490° C. and determine a molar selectivity ratio of ethylene to propylene after 30 minutes on-stream over the SAPO-34 catalyst.

Ex. 19

Replicate Ex 18, but substitute dimethylamine for monomethylamine and change the WHSV to 1.5 hr$^{-1}$ to keep carbon WHSV and the feed dilution ratio the same as in Ex 18.

Ex. 20

Replicate Ex. 18, substitute trimethylamine for monomethylamine and change the WHSV to 1.3 hr$^{-1}$ to keep carbon WHSV and the feed dilution ratio the same as in Ex 23.

Ex. 21

Replicate Ex 18, but change the catalyst to the H-ZSM-5 catalyst of Ex 2, the reaction temperature to 550° C. and evaluate molar selectivity ratio of ethylene to propylene after 300 minutes on stream.

Ex. 22

Replicate Ex 21, but substitute dimethylamine for mononunethylamine, and change the WHSV to 1.5 hr$^{-1}$.

Ex. 23

Replicate Ex 21, but substitute trimethylamine for monommethylamine, and change the WHSV to 1.3 hr$^{-1}$.

TABLE 3

| Ex. # | Catalyst | WHSV of total amines (hr$^{-1}$) | Time-on-stream (min) | Molar ratio of carbon to nitrogen in feed amine | Molar Selectivity of Ethylene to Propylene (%) |
|---|---|---|---|---|---|
| Ex. 18 | SAPO-34 | 2 | 30 | 1:1 | 1.43 |
| Ex. 19 | SAPO-34 | 1.5 | 30 | 2:1 | 1.55 |
| Ex. 20 | SAPO-34 | 1.3 | 30 | 3:1 | 1.65 |
| Ex. 21 | H-ZSM-5 | 2 | 300 | 1:1 | 0.44 |
| Ex. 22 | H-ZSM-5 | 1.5 | 300 | 2:1 | 0.47 |
| Ex. 23 | H-ZSM-5 | 1.3 | 300 | 3:1 | 0.48 |

The data and examples represented in Tables 2 and 3 show the general trend for either SAPO-34 or for H-ZSM-5, that the use of increasing content of $NH_3$ as a co-feed for a given amine, or the decrease of the hydrocarbon C:N ratio with or without a $NH_3$ co-feed, leads to a pronounced reduction in $C_2/C_3$ olefin product ratio. These examples demonstrate that one can design a process to control the $C_2/C_3$ olefin product ratio by controlling the feedstock N:C ratio by using a combination of $NH_3$ co-feed, a specific mixture of methylamines, or both.

What is claimed is:

1. A process for preparing an olefin, comprising placing at least one methylamine selected from monomethylamine, dimethylamine and trimethylamine, in a mixture with ammonia and methane in an amount sufficient to reduce the ratio of ethylene to propylene in the mixture of olefins and, optionally, an inert diluent, in contact with at least one microporous acidic silicoaluminophosphate catalyst or microporous aluminosilicate catalyst under conditions of temperature, pressure and weight hourly space velocity sufficient to convert at least a portion of the methylamine to a product stream comprising a mixture of olefins that comprises ethylene, propylene and butene.

2. The process of claim 1, wherein the temperature is within a range of from 400° centigrade to 700° centigrade.

3. The process of claim 1, wherein the pressure is sufficient to provide a total system pressure of from greater than or equal to 0.1 bar (10 kilopascals) to 60 bar (6 megapascals).

4. The process of claim 1, wherein the weight hourly space velocity of methylamine is within a range of from 0.1 grams of methylamine per gram of catalyst per hour to 50 grams of methylamine per gram of catalyst per hour.

5. The process of claim 1, wherein diluent is present in a mole ratio of diluent to methylamine that falls within a range of from greater than or equal to 0:1 to 20:1.

6. The process of claim 1, wherein the catalyst is selected from a group consisting of SAPO-34, H-ZSM-5, offretite, mordenite, 13X, and ferrerite.

7. The process of claim 1, wherein the at least one methylamine comprises a mixture of two or more of monomethylamine, dimethylamine and trimethylamine, the mixture having a carbon to nitrogen atom ratio greater than that of monomethylamine alone, whereby selectivity to a combination of ethylene and propylene is greater with the mixture than selectivity to such combination of ethylene and propylene based upon use of monomethylamine as a sole methylamine.

8. The process of claim 1, wherein at least a portion of ammonia, unreacted methylamine and, when present, diluent is recycled and mixed with fresh methylamine before the methylamine contacts the catalyst.

9. The process of claim 1, wherein the temperature is within a range of from 450° centigrade to 650° centigrade.

10. The process of claim 1, wherein the pressure is sufficient to provide a total system pressure of from 1 bar (100 kilopascals) to 5 bar (500 kilopascals).

11. The process of claim 1, wherein the weight hourly space velocity of methylamine is within a range of from 0.5 grams of methylamine per gram of catalyst per hour to 5 grams of methylamine per gram of catalyst per hour.

* * * * *